United States Patent
Ante et al.

(10) Patent No.: US 9,791,405 B2
(45) Date of Patent: Oct. 17, 2017

(54) OXYGEN SENSOR AND INTERNAL COMBUSTION ENGINE COMPRISING SAID SENSOR

(71) Applicants: Johannes Ante, Regensburg (DE); Andreas Wildgen, Nittendorf (DE)

(72) Inventors: Johannes Ante, Regensburg (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 176 days.

(21) Appl. No.: 14/401,017

(22) PCT Filed: Apr. 23, 2013

(86) PCT No.: PCT/EP2013/058338
§ 371 (c)(1),
(2) Date: Nov. 13, 2014

(87) PCT Pub. No.: WO2013/171033
PCT Pub. Date: Nov. 21, 2013

(65) Prior Publication Data
US 2015/0136095 A1    May 21, 2015

(30) Foreign Application Priority Data
May 14, 2012   (DE) .................. 10 2012 208 054

(51) Int. Cl.
| | |
|---|---|
| *G01N 31/12* | (2006.01) |
| *G01N 27/407* | (2006.01) |
| *F02M 35/10* | (2006.01) |
| *F02D 41/14* | (2006.01) |
| *F02M 26/22* | (2016.01) |

(Continued)

(52) U.S. Cl.
CPC ....... *G01N 27/4077* (2013.01); *F02D 41/144* (2013.01); *F02M 26/22* (2016.02); *F02M 26/45* (2016.02); *F02M 35/10373* (2013.01); *F02D 41/0072* (2013.01); *F02D 41/1454* (2013.01);
(Continued)

(58) Field of Classification Search
CPC .... G01N 27/4077; F02M 26/45; F02M 26/22; F02M 35/10373; F02M 35/1038; F02D 41/144; F02D 2041/285; F02D 41/0072; F02D 41/1454; F02D 2200/0406
See application file for complete search history.

(56) References Cited

U.S. PATENT DOCUMENTS

| | | |
|---|---|---|
| 4,283,261 A | 8/1981 | Maurer et al. |
| 4,823,760 A | 4/1989 | Nishida |

(Continued)

FOREIGN PATENT DOCUMENTS

| | | |
|---|---|---|
| DE | 28 55 012 A1 | 6/1980 |
| DE | 198 28 629 A1 | 2/1999 |

(Continued)

*Primary Examiner* — David Hamaoui
(74) *Attorney, Agent, or Firm* — Cozen O'Connor

(57) ABSTRACT

A sensor for detecting the oxygen content in the intake tract of an internal combustion engine includes: a sensor element having a measurement electrode; a metal cap that surrounds the sensor element; a heat dissipation element that connects the sensor element and the metal cap; and a bracket for the sensor element. The bracket is in the form of a plastic housing configured to accommodate evaluation electronics for the sensor element.

7 Claims, 1 Drawing Sheet

(51) Int. Cl.
*F02M 26/45* (2016.01)
*F02D 41/00* (2006.01)
*F02D 41/28* (2006.01)

(52) U.S. Cl.
CPC ............... *F02D 2041/285* (2013.01); *F02D 2200/0406* (2013.01); *F02M 35/1038* (2013.01)

(56) References Cited

U.S. PATENT DOCUMENTS

| | | | |
|---|---|---|---|
| 6,068,746 A * | 5/2000 | Kojima | G01N 27/407 204/421 |
| 6,182,639 B1 | 2/2001 | Igarashi et al. | |
| 6,266,997 B1 * | 7/2001 | Nelson | G01N 27/4077 204/426 |
| 6,418,779 B1 * | 7/2002 | Huang | G01N 27/4077 73/23.2 |
| 6,453,866 B1 | 9/2002 | Altmann et al. | |
| 6,779,392 B2 * | 8/2004 | Bell | G01L 17/00 73/146.8 |
| 7,267,117 B2 | 9/2007 | Tonetti et al. | |
| 7,593,828 B2 * | 9/2009 | Wang | F02B 37/24 701/31.4 |
| 7,690,262 B2 * | 4/2010 | Nakabayashi | G01K 1/18 73/708 |
| 8,001,827 B2 * | 8/2011 | Weyl | G01N 27/4077 73/23.31 |
| 8,806,918 B2 * | 8/2014 | Yonezu | G01N 27/4077 204/424 |
| 8,869,613 B2 | 10/2014 | Buschnakowski et al. | |
| 8,955,373 B2 * | 2/2015 | Duault | G01N 33/0037 73/114.69 |
| 2007/0044472 A1 | 3/2007 | Zhang | |
| 2009/0200164 A1 * | 8/2009 | Yoshikawa | G01N 27/4062 204/406 |
| 2012/0186564 A1 | 7/2012 | Vigild et al. | |

FOREIGN PATENT DOCUMENTS

| | | |
|---|---|---|
| DE | 10 2005 023259 A1 | 11/2006 |
| DE | 10 2005 062 774 A1 | 7/2007 |
| DE | 60 2004 012 986 | 6/2009 |
| DE | 10 2011 003095 A1 | 7/2012 |
| DE | 10 2011 088012 A1 | 6/2013 |
| DE | 10 2012 200062 A1 | 7/2013 |
| EP | 0 859 231 A1 | 8/1998 |
| EP | 1 139 096 | 10/2001 |
| EP | 1 213 473 A2 | 12/2002 |
| EP | 1 607 606 | 12/2005 |
| JP | 10-176577 | 6/1998 |
| JP | 2001-099688 | 4/2001 |
| JP | 2001-281214 | 10/2001 |
| JP | 2009-186424 | 8/2009 |
| JP | 2009-250682 | 10/2009 |
| JP | 2011-145267 | 7/2011 |
| JP | 2011-145268 | 7/2011 |
| JP | 2011-145269 | 7/2011 |

* cited by examiner

OXYGEN SENSOR AND INTERNAL COMBUSTION ENGINE COMPRISING SAID SENSOR

CROSS-REFERENCE TO RELATED APPLICATIONS

This is a U.S. national stage of application No. PCT/EP2013/058338, filed on 23 Apr. 2013, which claims priority to the German Application No. DE 10 2012 208 054.6 filed 14 May 2012, the content of both incorporated herein by reference.

BACKGROUND OF THE INVENTION

1. Field of the Invention

The present invention relates to a sensor for detecting the oxygen content in the intake tract of an internal combustion engine. The invention is also directed to an internal combustion engine having an oxygen sensor of this type.

2. Related Art

In internal combustion engines, it is, in many situations, desirable to detect the oxygen content in the intake air in the intake tract of the internal combustion engine. This is the case, for example, if the internal combustion engine is equipped with a facility for exhaust-gas recirculation into the intake tract. In this case, it is the intention to determine the exhaust-gas recirculation rate by detecting the oxygen content. Without exhaust-gas recirculation, the $O_2$ content in the intake air is approximately 21%, and this decreases with increasing exhaust-gas recirculation fraction.

According to the prior art, use is made here, as oxygen sensors, of conventional linear lambda probes such as are used in the exhaust tract of the internal combustion engine. Since such Lambda probes become very hot in the exhaust gas, they have an expensive housing that can withstand high temperatures. Therefore, in the prior art, cumbersome and expensive devices are used for measuring the oxygen fraction in the intake air.

SUMMARY OF THE INVENTION

It is an object of the present invention to provide a sensor for detecting the oxygen content in the intake tract of an internal combustion engine, which sensor is characterized by a particularly inexpensive construction.

This object is achieved according to an aspect of the invention by a sensor for detecting the oxygen content in the intake tract of an internal combustion engine, having a sensor element that has a measurement electrode, having a metal cap that surrounds the sensor element, having a heat dissipation element that connects the sensor element and metal cap, and having a bracket for the sensor element, the bracket being in the form of a plastic housing and accommodating the evaluation electronics for the sensor element.

In the case of the sensor design according to an aspect of the invention, the heat that is generated by the sensor element itself is dissipated via the heat dissipation element to the metal cap surrounding the sensor element, such that in this way, the bracket for the sensor element does not become too hot. The bracket is consequently not subjected to intense heat action, such that it can, according to the invention, be formed as a plastic housing. The invention is furthermore characterized in that the evaluation electronics for the sensor element are accommodated in the plastic housing, whereby the design is simplified further. Owing to the electronics being mounted directly on the sensor, the signal evaluation, in particular the storage of the corresponding characteristic curves, is made easier.

In addition to an oxygen sensor of this type, it is in many cases necessary for a pressure sensor to be provided in the air intake tract in order to measure the pressure prevailing in the air intake tract and enable corresponding pressure corrections to be performed on the basis of the measurement. In the case of the prior art, an additional pressure sensor with its own installation hole is provided as well as the oxygen sensor.

In a refinement of the invention, the sensor for detecting the oxygen content is configured so as to have an integrated pressure sensor. In this embodiment of the invention, therefore, use is made of a sensor design which has a combined oxygen sensor and pressure sensor. An additional, separate pressure sensor can therefore be dispensed with.

In the case of this design, the plastic housing of the oxygen sensor furthermore holds the sensor element of the pressure sensor. In a refinement, the plastic housing also accommodates the evaluation electronics for the pressure sensor.

The sensor element of the oxygen sensor comprises, in particular, an elongate plate-shaped support and a measurement electrode arranged thereon. Here, the sensor element extends coaxially with respect to the metal cap, which is provided with one or more openings so that the measurement electrode of the sensor element can come into contact with the intake air.

According to an aspect of the present invention, the heat generated by the sensor element itself is dissipated before it reaches the bracket for the sensor element. To achieve this, the heat dissipation element is provided, which heat dissipation element connects the sensor element to the metal cap that surrounds the sensor element with a spacing. Specifically, the heat dissipation element is, in this case, in the form of a plate-shaped element that surrounds the sensor element and that makes contact with the inner side of the metal cap. The heat dissipation element thus simultaneously forms a support element for the metal cap.

The bracket, which is in the form of a plastic housing, for the sensor element is preferably composed of epoxy resin and is preferably produced by transfer molding. This preferred embodiment ensures a very good sealing action, which is important for the corresponding sensor concept with low currents. Since the plastic housing accommodates the evaluation electronics, low costs are incurred because cable connections are dispensed with.

Another aspect of the present invention relates to an internal combustion engine having an air intake tract and having a charge-air cooler arranged therein. It is provided according to this aspect of the invention that the internal combustion engine has a sensor of the type described above, which sensor is arranged in the air intake tract between the charge-air cooler and the cylinder block of the internal combustion engine. The oxygen sensor designed according to the invention, or the combination of oxygen sensor and pressure sensor designed according to the invention, is thus arranged in the advantageous position downstream of the charge-air cooler. At this location, the temperatures are relatively low, such that the sensor bracket can be embodied in the form of a plastic housing. In the case of this positioning of the sensor, therefore, the bracket for the sensor element is not subjected to excessive heat action either by the gas stream to be measured or by the sensor element itself (as a result of the heat dissipation to the metal cap).

An aspect of the invention relates to an internal combustion engine having an exhaust-gas recirculation line into the air intake tract. Here, the sensor (oxygen sensor) serves for the detection of the exhaust-gas recirculation rate. It is self-evident that the sensor is arranged in the air intake tract downstream of the point at which the exhaust-gas recirculation line issues into the air intake tract.

The embodiment, according to the invention, of the bracket of the sensor element in the form of a plastic housing furthermore permits directional installation of the sensor in the air intake tract. In this way, the chances of overcoming water hammer problems are increased. Furthermore, the sensor designed according to the invention exhibits high water hammer resistance in any case, such that installation downstream of the charge-air cooler does not pose problems.

BRIEF DESCRIPTION OF THE DRAWINGS

The invention will be explained in detail below on the basis of an exemplary embodiment in conjunction with the drawings, in which.

DETAILED DESCRIPTION OF THE PRESENTLY PREFERRED EMBODIMENTS

Figure 1:
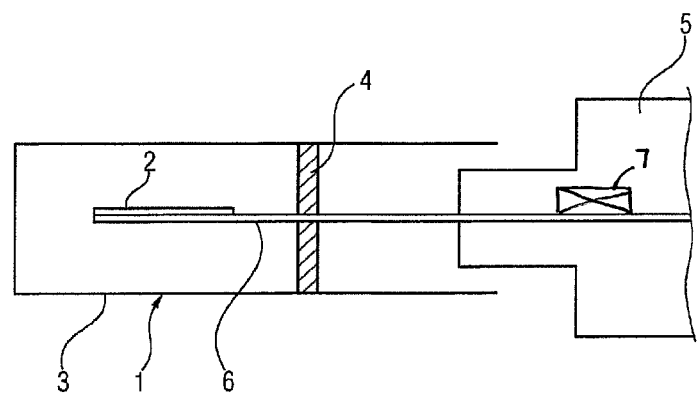
FIG. 1 shows a schematic longitudinal section through a sensor for detecting the oxygen content.

The sensor 1 only illustrated purely schematically in FIG. 1 has a sensor element 6 that comprises a bar-like support, on the front end of which there is arranged a measurement electrode 2. This may for example be an interdigital electrode. The conductor tracks of the measurement electrode extend, in FIG. 1, to the right as far as a contact region (not shown). A plastic housing 5 forms a bracket for the sensor element and has the evaluation electronics 7 for the sensor element.

The sensor element 6 is surrounded by a metal cap as a protective pipe 3. The sensor element 6 extends coaxially with respect to the metal cap, which is provided with multiple openings (not shown) so that the measurement electrode 2 of the sensor element 6 can come into contact with the intake air whose oxygen content is to be measured. The heat generated by the sensor element 6 itself is dissipated before reaching the plastic housing that forms the bracket 5 for the sensor element 6. For this purpose, a plate-shaped heat dissipation element 4 is provided, which connects the sensor element 6 to the metal cap. Here, the heat dissipation element 4 simultaneously serves as support element for the metal cap.

Figure 2:
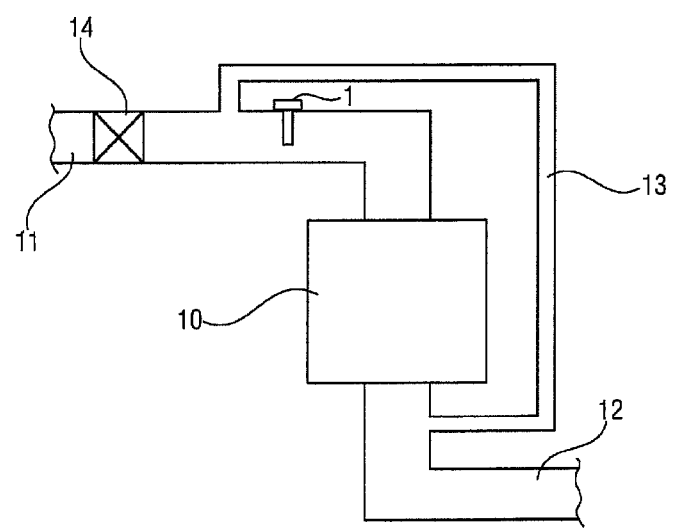
FIG. 2 shows a schematic diagram of an internal combustion engine with exhaust-gas recirculation and with a sensor arranged in the intake tract.

FIG. 2 schematically shows an internal combustion engine having a cylinder block 10, an air intake tract 11 and an exhaust tract 12. An exhaust-gas recirculation line 13 extends from the exhaust tract 12 to the air intake tract 11. A charge-air cooler 14 is also schematically illustrated in the intake tract 11.

The sensor 1 illustrated in FIG. 1 serves, in this embodiment, for measurement of the oxygen content in the intake air, and here, is arranged in the intake tract between the charge-air cooler 14 and the cylinder block 14 of the internal combustion engine, downstream of the point at which the exhaust-gas recirculation line 13 issues into the intake tract 11. Relatively low temperatures prevail at this location in the intake tract 11, such that the bracket 5 of the sensor element can be realized in the form of a plastic housing. Overall, it is the case here that the bracket 5 is not subjected to excessive heat action either by the sensor element 6 itself (as a result of the heat dissipation to the metal cap) or by the gas stream.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A sensor for detecting the oxygen content in the intake tract of an internal combustion engine, comprising:
   a sensor element having a measurement electrode at a first end;
   a metal cap formed as a pipe that surrounds the sensor element, the sensor element extending coaxially with respect to the pipe;
   a plate-shaped heat dissipation element, arranged in the pipe transverse to a longitudinal axis of the pipe, that extends radially from the sensor element and connects the sensor element and the metal cap and makes contact with an inner side of the metal cap and supports the metal cap;
   evaluation electronics for the sensor element arranged on a portion of the sensor element opposite the first end; and
   a bracket arranged opposite the measurement electrode into which the sensor element extends, the bracket being in the form of a plastic housing, the bracket accommodating the evaluation electronics for the sensor element arranged on the portion of the sensor element that extends into the bracket,
   wherein the plate-shaped heat dissipation element is arranged between the measurement electrode and the bracket to dissipate heat and is configured to be the support for the metal cap; and
   wherein the metal cap does not directly contact the bracket.

2. The sensor as claimed in claim 1, further comprising an integrated pressure sensor having a pressure sensor element.

3. The sensor as claimed in claim 2, wherein the plastic housing holds the pressure sensor element.

4. The sensor as claimed in claim 3, wherein evaluation electronics for the pressure sensor are arranged in the plastic housing.

5. The sensor as claimed in claim 1, wherein the sensor element comprises an elongate plate-shaped support and the measurement electrode is arranged on the elongate plate-shaped support.

6. An internal combustion engine having a cylinder block, an air intake tract, and a charge-air cooler arranged in the air intake tract, wherein said internal combustion engine has a sensor as claimed in claim 1, the sensor being arranged in the air intake tract between the charge-air cooler and the cylinder block of the internal combustion engine.

7. The internal combustion engine as claimed in claim 6, further comprising an exhaust-gas recirculation line into the air intake tract, wherein the sensor is configured to detect recirculation rate of exhaust-gas of the internal combustion engine.

\* \* \* \* \*